United States Patent [19]

Nickey et al.

[11] 4,452,632

[45] Jun. 5, 1984

[54] METHOD FOR THE APPLICATION OF TRIACONTANOL TO SOYBEANS TO ACHIEVE A SUBSTANTIAL INCREASE IN YIELD

[75] Inventors: Donald O. Nickey, Akron; Dane K. Parker, Massillon, both of Ohio

[73] Assignee: The Goodyear Tire & Rubber Company, Akron, Ohio

[21] Appl. No.: 434,798

[22] Filed: Oct. 18, 1982

[51] Int. Cl.$^3$ ..................... A01N 31/02; A01N 59/08
[52] U.S. Cl. .......................................... 71/122; 71/80
[58] Field of Search ................................... 71/122, 80

[56] References Cited

U.S. PATENT DOCUMENTS 4,150,970 4/1979 Ries ........................................ 71/122

4,333,758 6/1982 Welebir ................................... 71/80

OTHER PUBLICATIONS

Welebir, Chem. Abst., vol. 95, (1981), 216300g.

Primary Examiner—Catherine L. Mills
Attorney, Agent, or Firm—D. O. Nickey

[57] ABSTRACT

There is disclosed a method of treating soybeans with 1-triacontanol $CH_3(CH_2)_{28}-CH_2OH$, which produces a significant increase in yield. The method consists of applying a solution of "biologically active" 1-triacontanol at the proper: (1) stage of soybean plant maturity, (2) pH, (3) calcium content, (4) application rates and (5) number of applications; to attain a significant increase in yield. At least two foliar applied aqueous solutions of 1-triacontanol have been found to be effective.

2 Claims, No Drawings

METHOD FOR THE APPLICATION OF TRIACONTANOL TO SOYBEANS TO ACHIEVE A SUBSTANTIAL INCREASE IN YIELD

FIELD OF THE INVENTION

This invention relates to a plant growth regulator and more particularly to a specific formulation and application rate of 1-triacontanol as a soybean yield enhancer.

BACKGROUND ART

In 1975 it was reported by Dr. S. K. Ries, in the *Michigan Agricultural Experimental Station Journal Article*, No. 7431, that coarsely chopped alfalfa hay when applied to the soil as a band adjacent to a crop row could improve plant growth. This phenomenon was mentioned with respect to lettuce, rice, cucumbers, tomatoes, cauliflower, and field corn. In an article that appeared in *Science*, Mar. 25, 1977, Volume 195, pages 1339 through 1341, Ries and his coworkers reported the isolation of triacontanol as the active growth agent that had been present in the earlier alfalfa work and laboratory scale foliar application to field corn of a solution containing 0.01 milligram per liter up to 1.00 milligram of triacontanol per liter was reported.

Biological activity of 1-triacontanol has been shown to be extremely sensitive to its method of synthesis. This observation is believed to be a function of the amount and type of impurities derived from the synthetic method, i.e. different methods produce different amounts and types of impurities, some of which are potent inhibitors. (See Jones J., Wert F. V., Ries, S. K., *Planta* 144: 277–292 (1979).

U.S. Pat. No. 4,150,970, S. K. Reis and C. C. Sweeley, discloses and claims the use of 1-triacontanol as a growth regulator for plants. Specifically claimed is a method for stimulating the growth of a plant selected from rice, wheat, corn tomatoes or barley, by applying thereto an effective amount of 1-triacontanol. The means of application can be a foliar spray, a soil drench, a side dressing or as part of an insecticide or fertilizer application.

U.S. Pat. No. 4,167,641 describes a process for the preparation of triacontanol.

U.S. Pat. No. 4,367,346, issued Jan. 4, 1983 by one of the present inventors discloses a new method for the synthesis of 1-triacontanol.

U.S. Pat. No. 4,230,485 discloses a method for the treatment of field corn with triacontanol. This patent teaches that the stage of plant maturity is the key to the attainment of increased yields in field corn. Foliar applied rates from about 2 milligrams to about 56 milligrams per acre were found to be equally effective. The dissolution of triacontanol in chloroform was found to be an effective procedure but acetone was found to be a more effective solvent. Other solvents such as the amyl alcohols were speculated to be equally or more effective.

U.S. Pat. No. 4,299,618 discloses that soybean crop yield can be increased by the foliar application of small amounts of trialkyl 2,4-dichlorobenzylammonium chlorides during certain stages of growth. Application to northern intermediate varieties at a rate of about 0.25 to 0.5 pounds (0.11 to 0.23 Kgs) per acre during the 5–8 trifoliate leaf stage was disclosed. Application to the southern varieties at a rate of about 0.5 to 0.75 pounds (0.23 to 0.34 Kgs.) per acre during the 10 to 11 trifoliate leaf stage was found to be satisfactory.

Numerous investigators have attempted to increase the yield of soybeans through application of 1-triacontanol. At present the yield increases in soybeans have been either nonexistent or erratic. As soybean production is an important part of the American agricultural industry, it is evident that a method which can substantially increase the yield of soybeans through use of 1-triacontanol would be highly desirable. No reference has been found that is concerned with increasing, specifically soybean crop yield. Most significantly, no reference teaches the optimum times, rates of application, timing of application, number of applications and attendant spray solution preparation that can effectively and dramatically increase the yield of soybeans.

DISCLOSURE OF THE INVENTION

There is disclosed a method for increasing soybean crop yield that comprises applying to the foliage of soybean plants small amounts of 1-triacontanol in an aqueous spray, wherein said aqueous spray comprises (a) between 0.0001 g to 1 g of 1-triacontanol per cubic meter of water, (b) at least 75 grams of calcium chloride per cubic meter of water, and (c) at a pH of at least 10 but less than 12; said aqueous spray being applied at least twice at the foliage of the soybeans at a rate of at least $1.5 \times 10^{-5}$ cm$^3$ of spray solution per square meter.

The second and or subsequent applications should be made after the prior application has had an opportunity to dry. This timing factor obviously depends upon temperature, humidity, and wind conditions.

This invention is particularly directed to a method for increasing soybean crop yield which comprises contacting soybean plants with an effective spray composition containing 1-triacontanol in sufficient amount and number of applications to increase soybean yield. Foliar applications of the spray solution are preferable. The amount of triacontanol applied can vary dependent upon the variety of soybean involved.

1-triacontanol, which is used in this invention, is most conveniently applied in conjunction with a liquid carrier containing a minor amount of said compound. Since 1-triacontanol is insoluble in water, it has been determined that dissolution of the appropriate amount of 1-triacontanol into acetone, which is thereafter added to the water, is preferred. In general, almost any inert liquid solvent or carrier material may be used as long as it is capable of dissolving or dispersing the triacontanol and the calcium chloride.

Surface active agents (i.e. film forming agents as exemplied by mineral and ester waxes and natural and synthetic resins and polymers) are not used.

In carrying out the method of this invention the spray solution may be applied in various ways. Preferably, the spray solution is in the form of an aqueous dispersion. In practice, 1-triacontanol is applied as a dilute solution in conjunction with calcium chloride at the proper pH to all the leaves, i.e. foliar application.

The rate of application is expressed in terms of milligrams of triacontanol per sq. meter. The spray rate depends upon the concentration of the triacontanol spray solution, the variety of the soybean and the growth stage of the plant.

The process of the present invention provides specific parameters under which triacontanol can be applied to soybean to obtain maximum grain yield enhancement.

DESCRIPTION OF THE INVENTION

The synthetic of 1-triacontanol has been described in U.S. Pat. No. 4,167,641. Also, triacontanol has been isolated from alfalfa plants. However, the 1-triacontanol used in these experiments was prepared according to a method described in U.S. Pat. No. 4,367,346 issued Jan. 4, 1983.

Generally, the process described in U.S. Pat. No. 4,367,346 can be used to synthesize long chain carbon compounds. The Patent 4,367,346 synthesis route consists of: (a) reacting cyclododecanone with morpholine in the presence of a catalyst to form 1-morpholino-1-cyclododecene; (b) separating the 1-morpholino-1-cyclododecene and reacting it with an organic acid halide of 15-20 carbon atoms in the presence of a tertiary amine in an organic solvent while maintaining the reaction temperature at 0°-10° C. followed by (c) hydrolysis under acidic conditions, thereafter (d) separating the 2-n-alkyl-cyclotetradecanedione and reacting with a solution of alkali metal hydroxide and diethylene glycol at 90°-110° C. followed by (e) addition of hydrazine hydrate and the reaction mixture is refluxed at 125°-135° C., thereafter (f) the distillate is removed until the temperature of the reaction mixture climbs to 190°-210° C. where it is refluxed for 3 to 20 hours with slow stirring, and then (g) cooled to 110°-125° C. followed by addition of hot (80°-95° C.) water with rapid stirring followed by (h) neutralization with aqueous acid to a pH of 2 to yield the carboxylic acid which is separated and purified by recrystallization which is then (i) dissolved in tetrahydrofuran under an inert atmosphere and has added thereto the reducing agent, borane-methyl sulfide complex with stirring and heated to 40°-65° C. for 2 to 3 hours before cooling to ambient temperature followed by the sequential addition of ethanol and water to quench excess borane reagent followed by (k) separation and purification of the long chain alcohol.

The following examples are presented to illustrate the invention and are not intended to limit the scope of the present invention. The following example describes the synthesis of 1-triacontanol used in Examples 2 and 3.

EXAMPLE 1

Step 1

Preparation of 1-Morpholino-1-Cyclododecene

A two liter three-necked flask was charged with 366 grams (2.0 moles) cyclododecanone, 348 grams (4.0 moles) morpholine, 600 ml toluene and 3.0 grams (0.0158 moles) para-toluene sulfonic acid catalyst. A magnetic stir bar was added along with a few carbon boiling chips. A Dean-Stark water trap and condenser were then attached and the mixture brought to reflux with stirring. After 46 hours reflux, 75 ml. of aqueous phase had been collected. The mixture was then cooled and the excess toluene and morpholine removed at reduced pressure (25-50 mm Hg). The residue was then distilled under vacuum (0.6 mm Hg) to yield 300.5 grams of a viscous clear oil, 1-morpholino-1-cyclododecene, b.p. 135°-150° C., 60% yield.

Step 2

Preparation of Stearoyl Chloride

A two liter three-necked flask was charged with 570 grams (2.0 moles) acetic acid. The flask was then equipped with a mechanical stirrer, nitrogen inlet and thermometer in a fume hood. The system was then purged with a slow bleed of nitrogen and 163 ml (2.23 moles) of thionyl chloride and 3 ml (0.04 moles) of dimethyl formamide catalyst were added. The mixture was slowly warmed over one hour to 65° C. All the solid slowly dissolves during this period to yield a clear yellow liquid (HCl and $SO_2$ evolved). Heat was removed and the mixture was allowed to stand at room temperature overnight under nitrogen. Strip off under vacuum excess thionyl chloride and dimethyl formamide catalyst to obtain 580 grams of stearoyl chloride (95.7% yield) as a clear brownish liquid.

Step 3

Preparation of 2-n-hexadecyl-cyclotetradecanedione

A three liter three-necked flask was charged with 356.6 grams (1.42 moles) of 1-morpholino-1-cyclododecene and 153.5 grams (1.52 moles) triethylamine. The flask was then equipped with a mechanical stirrer, nitrogen inlet, thermometer and a dropping funnel. A solution of 390.4 grams (1.22 moles) of stearoyl chloride in 250 ml of methylene chloride was then placed in the dropping funnel. The reaction flask was cooled to 0°-5° C. and the stearoyl chloride solution added over 5½ to 6 hours with the temperature kept between 5°-10° C. After the addition was complete, the mixture was allowed to stand at room temperature overnight.

This was followed by the addition with stirring of 500 ml of 5 N hydrochloric acid and 600 ml of methylene chloride. One-half gram of the phase-transfer catalyst n-hexadecyl-tri-n-butyl phosphonium bromide was then added and the mixture refluxed for two hours to complete the hydrolysis. The methylene chloride layer was then separated out and the solvent allowed to evaporate to yield 615.5 grams of the crude product. Gas chromatographic analysis indicates a composition of approximately 69 percent diketone, 17.5 percent cyclododecanone and 2.5 percent stearic acid. The addition of the phase-transfer catalyst, n-hexyl-decyl tri-n-butyl phosphonium bromide was used to promote the reaction, however, the reaction will proceed without a catalyst. The product is conveniently purified at this stage by multiple recrystallization from ethanol. The recrystallized material is then used in the next step.

Step 4

Preparation of 1-Triacontanoic Acid

A two liter three-necked flask equipped with a mechanical stirrer, thermometer, nitrogen inlet and dropping funnel was charged with 126.15 grams 2-n-hexadecyl-cyclotetradecanedione, 350 ml diethylene glycol, 66.0 grams (≐1.0 mole) potassium hydroxide pellets and 5 ml ethanol. The mixture was then warmed under nitrogen with stirring to 110° C. for 1½ to 2 hours. After this period, 60 ml (≐1.0 mole) of 85 percent hydrazine hydrate was added all at once and the temperature raised to reflux (127°-132° C.) for 18 hours. A Dean-Stark trap was then attached. Distillate was slowly removed until the temperature of the reaction mixture had climbed to 210°-220° C. Once at this temperature, the trap was removed and the mixture refluxed at this temperature for 18 hours with slow stirring. The reaction mixture was then cooled to 110°-125° C. and 750 ml of hot water (80°-90° C.) was carefully added with rapid stirring. This was followed by the addition over 10 minutes of 250 ml of 5 N hydrochloric acid. The pH of the mixture at this point is between 0 and 2. The crude 1-triacontanoic acid can be conveniently purified by multiple recrystallization from methyl ethyl ketone. 80.66 grams was isolated after recrystallization, for 91.8 percent yield (based on 69 percent purity of starting 2-n-hexadecyl-cyclotetradecanedione). The addition of 5 ml of ethanol was used to promote the reaction, however, the reaction will proceed without the addition of ethanol. Applicant candidly discloses the use of ethanol as the best mode in synthesizing the 1-triacontanoic acid.

Step 5

Preparation of 1-Triacontanol

A five liter three-necked flask equipped with mechanical stirrer, nitrogen inlet, septum inlet, thermometer and condenser was charged with 182.0 grams (0.402 moles) recrystallized 1-triacontanoic acid and 1900 ml of tetrahydrofuran. The system was continuously purged with a slow nitrogen stream while being warmed to 35° C. At this temperature, 75 ml (0.75 moles) of 10 M borane-methyl sulfide complex was added over a thirty minute period via a long needle syringe. After the addition, the mixture was stirred three hours at 45° C. then warmed to 65° C. for one hour before cooling to room temperature ($\doteq$25° C.). 250 ml of methanol was then carefully added over thirty minutes followed by the addition of 150 ml of water over fifteen minutes. The quenched mixture was then poured into excess of cold water and left to stand in a fume hood overnight. The crude product was filtered off and dried in a circulating air oven at 50° C. to yield 147.0 grams crude 1-triacontanol. Gas chromatographic analysis of the crude product indicated a composition of 89.3 percent 1-triacontanol, 1.5 percent octacosanol and 5.2 percent 1,13-triacontandiol.

The crude 1-triacontanol (89.3 percent purity) could be readily purified by placing 50.0 grams of crude material in a cellulose extraction thimble and extracting it continuously in a soxhlet apparatus with boiling hexane (1250 ml hexane volume). After 2–3 hours extraction all the triacontanol had been removed from the thimbles. A magnetic stir bar was then added to the hot hexane solution and the mixture stirred in air until reaching ambient conditions. During this period 1-triacontanol crystallized out of the mixture. 35.3 grams of 1-triacontanol was isolated by filtration and analyzed to be 96.6 percent pure 1-triacontanol, 1.3 percent octacosanol and 0.5 percent 1,13-triacontanediol.

In a purification of 1-triacontanol by recrystallization a ratio of 50 grams of crude 1-triacontanol into 800 ml to 3000 ml hexane is appropriate with the preferred amount being 1,250 ml. The solution is cooled slowly with stirring to room temperature and the recrystallized 1-triacontanol is filtered off.

EXAMPLE 2

Spray Solution Preparation

One hundred milligrams of 1-triacontanol, prepared in Example 1 was dissolved in one gallon (3.785 liters) of acetone. The acetone/triacontanol solution was then added to 207 gallons (783.5 liters) of $H_2O$ that was in the tank of a commercial field spraying unit. Approximately 63 grams of $CaCl_2$ was added to the tank and a circulating pump was started to begin mixing. Later laboratory analysis determined that the solution contained 1.95 mM of $Ca^{++}$. The pH of the spray solution was then adjusted with concentrated aqueous NaOH to a 9.0 plus on litmus paper. Laboratory analaysis determined that the spray pH was 10.5. The spray solution was then transported to the test field with continued mixing.

EXAMPLE 3

Field Preparation

The preparation and application of the spray solution was conducted as if commercially available herbicides and pesticides were used. The test field was located in Putman County, Ohio. The test field was of the Pauling clay and Roselms soil type. A variety of soybean known as SRF 307P was planted on June 8, 1981. The soil had been fertilized with 4-12-24 fertilizer with 3 percent Zn at 260 pounds per acre. The soybean seed was planted using a commercial planter. At the end of June 1981 flooding of the test field (due to severe rain) caused an approximate 50% loss of the first planting. A second planting on July 4, 1981 of a soybean seed variety known as Gold Tag 1330 was inserted between the rows of the June 8th planting.

On July 14, 1981 the spray solution of Example 2 was prepared and applied at a rate of approximately 20 gallons (0.075 $m^3$) per acre as a foliar spray with full leaf contact. An area measuring approximately 300 feet (91.4 m) by 1212 feet (370 m), the 1212 foot measurement being the row length, was sprayed at the 20 gallons (0.075 $m^3$) per acre (4046.9 $m^2$) rate with the air temperature at 78°–80° F. (25°–27° C.) under a clear sky at 11:15 A.M., E.D.T. Approximately 20 minutes after application the spray solution had dried on the soybean leaves. An area measuring approximately 80 by 1312 feet (24.4 m by 400 m) (2.03 acres) that had just been sprayed (the solution had dried on the leaves) was sprayed again at approximately 20 gallons (0.075 $m^3$) per acre rate. Each of these areas were staked off.

The field testing design consisted of a field approximately 23.6 acres in size, with three plots staked off. The field sides and ends were not used. Plot No. 1 was 6.43 acres (2.6×$10^4$ $m^2$) in size and measured 370 m by 70.5 m. Plot No. 1 was sprayed with the solution at a rate of 9.5 mg of triacontanol per acre (4046 $m^2$).

Plot No. 2 was 2.03 acres (8.2×$10^3$ $m^2$) in size and measured 370 m by 22.3 m. Plot No. 2 was sprayed twice with the solutiion for a rate of 19 mg of triacontanol per acre (4046 $m^2$).

Plot No. 3 was 5.34 acres (2.16×$10^4$ $m^2$) in size and measured 370 meter by 58.6 meters. Plot No. 3 was not sprayed with the triacontanol solution and was thus the control.

The spraying of the solution from Example 2 was done by a commercial spray unit mounted on a pickup truck. Since the second planting was placed between the rows of the first planting it was impossible to totally avoid damage to some of the plants. The spray truck had spray booms much wider than the width of the truck wheel base, thus minimizing damage to the soybeans, however, Plot No. 2 which received two sprayings had the most damage.

The test field was not cultivated or fertilized after the spraying of the triacontanol solution. On Nov. 4, 1981 the test field was harvested using a commercial combine with the proper head and adjustments for soybean harvesting. The harvest from each plot was placed in a wagon, weighed, and then the weight of the wagon subtracted to obtain net soybean weight. Bean moisture was also determined by means accepted within the agricultural community.

The data generated from the harvest can be found in Table I. Table I sets out by Plot number the net weight moisture content, total bushels and bushels per acre of the soybeans.

TABLE I

| | Harvest Data | | |
|---|---|---|---|
| | Plot #1 | Plot #2 | Plot #3 |
| Area (acres) | 6.43 | 2.03 | 5.43 |
| Net Soybean wt. (lbs) | 9610 | 6160 | 8570 |
| Bean Moisture (%) | 14.7 | 15.1 | 14.4 |
| Total Bushels | 153.64 | 97.54 | 138.0 |
| Bushels/acre | 23.9 | 48.0 | 25.8 |
| % Yield Change From Control (Plot #3) | −7.4 | +86.0 | — |

Table I amply demonstrates the unpredicted benefits that are obtained when a second application of the triacontanol solution is made. The −7.4% yield change of Plot No. 1, in view of the control, can be explained by the damage caused by the truck mounted spray unit.

Two linear feet of soybean plants from each planting were collected from each test plot. The numbers, pods per sample, and the other data was manually obtained and is presented in Table II.

TABLE II

| | Raw Data From Two Linear Feet of Plantings | | |
|---|---|---|---|
| | Plot #1 | Plot #2 | Plot #3 |
| No. Plant Stalks | 23 | 15 | 13 |
| No. One bean pods | 57 | 44 | 30 |
| No. Two bean pods | 133 | 166 | 108 |
| No. Three bean pods | 218 | 280 | 159 |
| No. Four bean pods | 66 | 5 | 1 |
| Total Number Pods | 474 | 495 | 298 |
| Total Number Beans | 1241 | 1236 | 727 |
| Total bean wt. (gms) | 202.85 | 211.1 | 121.0 |
| Total wt. stalks (gms) | 119.0 | 108.2 | 77.2 |
| Average Bean wt. (gms) | 0.164 | 0.171 | 0.166 |
| Average Stalk wt. (gms) | 5.2 | 7.2 | 5.0 |
| Average No. beans/stalk | 54 | 82 | 56 |
| Average % Diff. over Control | −3.6 | +46.4 | — |
| Average bean wt (gms/stalk) | 8.8 | 14.1 | 9.3 |
| Average % Diff. over Control | −5.4 | +51.6 | — |

Again Table II indicates that duel sprayings have an unexpected advantage over single spraying in this formulation on these plants. The −5.4% difference of Plot No. 1 in light of the control (Plot No. 3) can be explained by the damage caused by the truck mounted spray unit.

This large scale, field test of 1-triacontanol indicates that 1-triacontanol can be an extremely effective growth promoter when properly formulated and applied. Soybeans produce larger plants with more beans per plant when 1-triacontanol is applied according to the present invention. The double application of the spray solution to soybeans produced the greatest increase ever reported for soybeans.

Industrial Applicability

The application of the present invention to the commercial production of soybeans while have a great impact on agricultural community. Greatly increased yields per acre, of a valuable agricultural commodity such as soybeans, will have a vast and far reaching effect on the world as a whole.

While certain representative embodiments and details have been shown for the purpose of illustrating the invention, it will be apparent to those skilled in this art that various changes and modifications may be made therein without departing from the scope of the invention.

I claim:

1. A method for increasing soybean crop yield that comprises applying to the foliage of soybean plants small amounts of 1-triacontanol, wherein the 1-triacontanol is prepared by:
   (a) reacting cyclododecanone with morpholine in the presence of a catalyst to form 1-morpholino-1-cyclododecene;
   (b) separating the 1-morpholino-1-cyclododecene and reacting it with stearoyl chloride in the presence of a tertiary amine in an organic solvent while maintaining the reaction temperature of 0°–10° C. followed by;
   (c) hydrolysis under acidic conditions, thereafter
   (d) separating the 2-n-hexadecyl-cyclotetradecanedione, reacting with a solution of alkali metal hydroxide in diethylene glycol at 90°–110° C. followed by
   (e) addition of hydrazine hydrate and refluxing the reaction mixture at 125°–135° C., thereafter removing
   (f) the distillate until the temperature of the reaction mixture climbs to 190°–210° C. then refluxing for 3 to 20 hours with slow stirring, and then
   (g) cooling to 110°–125° C. followed by addition of hot (80°–95° C.) water with rapid stirring followed by
   (h) neutralization with aqueous acid to a pH of 2 to yield triacontanoic acid which is separated and purified by recrystallization which is then
   (i) dissolved in tetrahydrofuran under an inert atmosphere and has added thereto the reducing agent, borane-methyl sulfide complex with stirring and heated to 40°–45° C. for 2 to 3 hours before cooling to ambient temperature followed by the sequential addition of methanol and water to quench excess borane reagent followed by
   (k) separation and purification of the triacontanol; said 1-triacontanol is in an aqueous spray, wherein said spray comprises (1) 0.0001 g to 1 g of 1-triacontanol per cubic meter of water, (2) at least 75 grams of calcium chloride per cubic meter of water, and (3) at a pH of at least 10 but less than 12; said aqueous spray being applied at least twice to the foliage of the soybeans at a rate of at least $1.5\times10^{-5}$ $m^3$ of spray solution per square meter.

2. A method according to claim 1 for the foliar application of 1-triacontanol to soybeans which consists of (1) 0.0001 g to 1 g of 1-triacontanol dispersed with 1 $meter^3$ of $H_2O$, (2) at least 75 grams of calcium chloride per cubic meter of water, and (3) at a pH of 10.5 to 11.5 adjusted through addition of sodium hydroxide.

* * * * *